United States Patent [19]
Gordon et al.

[11] Patent Number: 5,601,980
[45] Date of Patent: Feb. 11, 1997

[54] MANUFACTURING METHOD AND APPARATUS FOR BIOLOGICAL PROBE ARRAYS USING VISION-ASSISTED MICROPIPETTING

[75] Inventors: Gary B. Gordon, Saratoga; Scott A. Conradson, Los Altos Hills; Kay Lichtenwalter, San Jose, all of Calif.

[73] Assignee: Hewlett-Packard Company, Palo Alto, Calif.

[21] Appl. No.: 311,374

[22] Filed: Sep. 23, 1994

[51] Int. Cl.$^6$ ................................................. G01N 35/10
[52] U.S. Cl. .................... 435/6; 435/286.2; 435/286.4; 435/286.5; 435/309.1; 435/283.1; 422/63; 422/100; 436/55; 436/63; 436/807; 436/809
[58] Field of Search ................................ 422/63, 100, 67; 436/54, 55, 63, 807, 809; 435/287, 289, 416

[56] References Cited

U.S. PATENT DOCUMENTS

| | | | |
|---|---|---|---|
| 3,783,696 | 1/1974 | Coleman | 422/100 |
| 4,452,899 | 6/1984 | Alston | 436/46 |
| 4,919,899 | 4/1990 | Hermann et al. | 422/245 |
| 5,143,849 | 9/1992 | Barry et al. | 436/50 |
| 5,275,951 | 1/1994 | Chow et al. | 436/50 |
| 5,334,353 | 8/1994 | Blattner | 422/100 |
| 5,336,467 | 8/1994 | Heidt et al. | 422/64 |
| 5,338,688 | 8/1994 | Deeg et al. | 436/180 |
| 5,443,791 | 8/1995 | Cathcart et al. | 422/65 |

*Primary Examiner*—James C. Housel
*Assistant Examiner*—Rachel Heather Freed

[57] ABSTRACT

A method and apparatus is provided for spotting a biological probe onto an array. A micropipette containing a quantity of the biological probe in solution is manipulated to a position above a selected location within the array. The micropipette is pressurized sufficiently to produce a droplet of the biological probe at an open tip of the micropipette. Formation of the droplet is simultaneously visually monitored during the pressurization of the micropipette in order to estimate a volume measurement of the droplet. Upon reaching a predetermined volume for the droplet, the pressurizing of the micropipette is discontinued. The droplet of the predetermined volume is then dispensed onto the selected location.

20 Claims, 3 Drawing Sheets

5,601,980

MANUFACTURING METHOD AND APPARATUS FOR BIOLOGICAL PROBE ARRAYS USING VISION-ASSISTED MICROPIPETTING

BACKGROUND OF THE INVENTION

1. Field of the Invention

The invention relates to the use of biological or chemical compounds for the detection of the presence of other biological or chemical compounds within a specimen, and more particularly, to a method and apparatus for "spotting" the differing compounds onto a test array.

2. Description of Related Art

Biological or chemical compounds (commonly referred to as "probes") are commonly used as reagents in the detection of other target biological or chemical compounds, such as certain viruses or bacteria, within a specimen under test. Any such target compounds existing within the specimen can be identified though the controlled exposure of the specimen to the probe and the detection of DNA hybridization or antibody-antigen reactions. For example, the binding between an antibody and molecules displaying a particular antigenic group on their surface may be used as a basis for detecting the presence of the antibody, molecules carrying the antigenic group, or the antigenic group itself. Distinct varieties of reagent probes can be specifically formulated to detect particular target compounds. Accordingly, the specimen can be evaluated for the presence of a wide assortment of target compounds by exposure to a variety of probe types.

In particular, the probe may contain biological material having target DNA of up to a thousand base pair in length. Upon controlled exposure of a specimen having a biological match with the target DNA, the specimen and target DNA hybridize, or bind together. The presence of the target DNA within the specimen is detected by evaluation of whether the hybridization has occurred. The target DNA can be labelled with fluorescent tags that can be detected by exposure to particular wavelengths of light, such as ultra-violet light. Optical detection of the fluorescent emission from the probe indicates that the specimen has hybridized with the probe.

To prepare a test using a particular probe, a small quantity of the probe in solution is dispensed onto a prepared glass slide or other test surface, a process referred to as "spotting." The specimen is then exposed to the spotted probe and the specimen permitted to selectively hybridize with the probe. After excess specimen material has been rinsed off the test surface, any hybridization with the probe can be readily detected. Probe tests of this nature represent a relatively simple and cost effective method for clinically evaluating a specimen.

A drawback of the conventional probe test method is that it can be time consuming and cumbersome in situations in which the detection of numerous target compounds is desired. Typically, it is desirable to evaluate a specimen for the presence of a wide assortment of target biological and/or chemical compounds. In these situations, separate probe tests for each target compound would have to be conducted. To avoid this unnecessary duplication of effort and expense, a possible solution would be to utilize a single test slide that is pre-spotted with an assortment of probes, and to expose the specimen to all the probes simultaneously. This way, reactions of each of the probes to the specimen can be identified during a single procedure.

This solution is severely limited, however, by practical aspects of spotting the probe onto the slide. To prepare a test slide pre-spotted with a large number of probes, each of the probes must necessarily have a rather minuscule volume, such as on the order of one nanoliter. Spaces should be provided between adjacent ones of the probes to prevent undesired mixing of the probes. An additional consideration is that the amount of specimen material that ultimately hybridizes with the probes at the particular spots depends, in part, on the volume of the probe dispensed at the spot. Thus, the volume of the probe must be precisely controlled.

A secondary problem with conventional probe spotting is the control of probe placement on the test slide. The positional accuracy of the placement of the probes onto the test slide is critical to accurate correlation of detected hybridization with a particular probe. Due to the extremely small volume of the probe dispensed onto the test slide, the placement accuracy should be within the sub-millimeter range.

Another drawback with conventional probe spotting that relates to the probe placement problem is the difficulty in preventing false negatives. Due to the relatively low accuracy of conventional spotting techniques, a probe spot can be placed in an incorrect position on a test slide, or a probe can be inadvertently omitted from the test slide altogether. In a test of a specimen in which a particular probe fails to hybridize with a specimen, the normal conclusion to be drawn is that the specimen is negative with respect to the existence of a particular target compound. This conclusion would be erroneous, however, if the probe had not been properly spotted onto the test slide.

The accurate dispensing of small volumes of liquid has been previously demonstrated in conventional ink-jet printers. The cartridges utilized in ink-jet printers dispense a controlled volume of ink onto a paper substrate by use of a pressure wave created within the cartridge. Nevertheless, this approach would not be applicable to probe spotting, since the pressure wave results from a sharp temperature increase to the ink that would otherwise damage or sheer the probe due to the inherent fragility of the probe. Further, the ink-jet cartridges produce a high degree of splattering that is acceptable for printing applications, but would risk contamination of adjacent probe spots in this application. Thus, the conventional ink-jet technology would not be a feasible method for measuring and controlling the accurate placement of probes of such small fluid volumes.

Therefore, a critical need exists for a method and apparatus for accurately spotting minuscule volumes of biological probes in solution onto a test slide. Such a method should provide for precise control over probe volume, as well as placement. The method should also be cost effective and readily adaptable for large scale production of test slides having relatively high numbers of individual probes.

SUMMARY OF THE INVENTION

In accordance with the teachings of this invention, a novel method and apparatus for spotting a biological probe onto an array is provided. In the invention, the probe spotting is controlled by use of a vision-assisted automation process.

A micropipette containing a quantity of the biological probe in solution is manipulated to a position above a selected location within the array. The micropipette is pressurized sufficiently to produce a droplet of the biological probe at an open tip of the micropipette. Simultaneously with the formation of the droplet, the droplet is visually monitored and a volume measurement of the droplet is estimated. Upon reaching a predetermined volume for the droplet, the pressurizing of the micropipette is discontinued. The droplet of the predetermined volume is then dispensed onto the selected location. Visual monitoring is also used to estimate the position of the tip of the micropipette in relation to indices disposed on the array.

An apparatus for spotting a biological probe onto an array comprises a micropipette containing a quantity of the biological probe in solution. The micropipette is selectively manipulated to a location within the array. A pressure source is provided in communication with the micropipette, and a droplet of the biological probe is produced at an open tip of the micropipette by application of pressure from the pressure source. A volume measurement of the droplet is estimated and application of the pressure is discontinued upon reaching a predetermined volume for the droplet. The droplet volume is estimated by visually monitoring formation of the droplet, such as by a video camera or a linear charge coupled device (CCD) array. The droplet position is estimated by visually monitoring the tip of the micropipette in relation to indices disposed on the array.

A more complete understanding of the manufacturing method and apparatus for biological probe arrays using vision-assisted micropipetting will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

This invention provides a method and apparatus for accurately spotting minuscule volumes of biological probes in solution onto a test slide. The method provides for precise control over probe volume as well as placement. Further, the method is cost effective and readily adaptable for large scale production of test slides having high numbers of individual probes.

Figure 1:
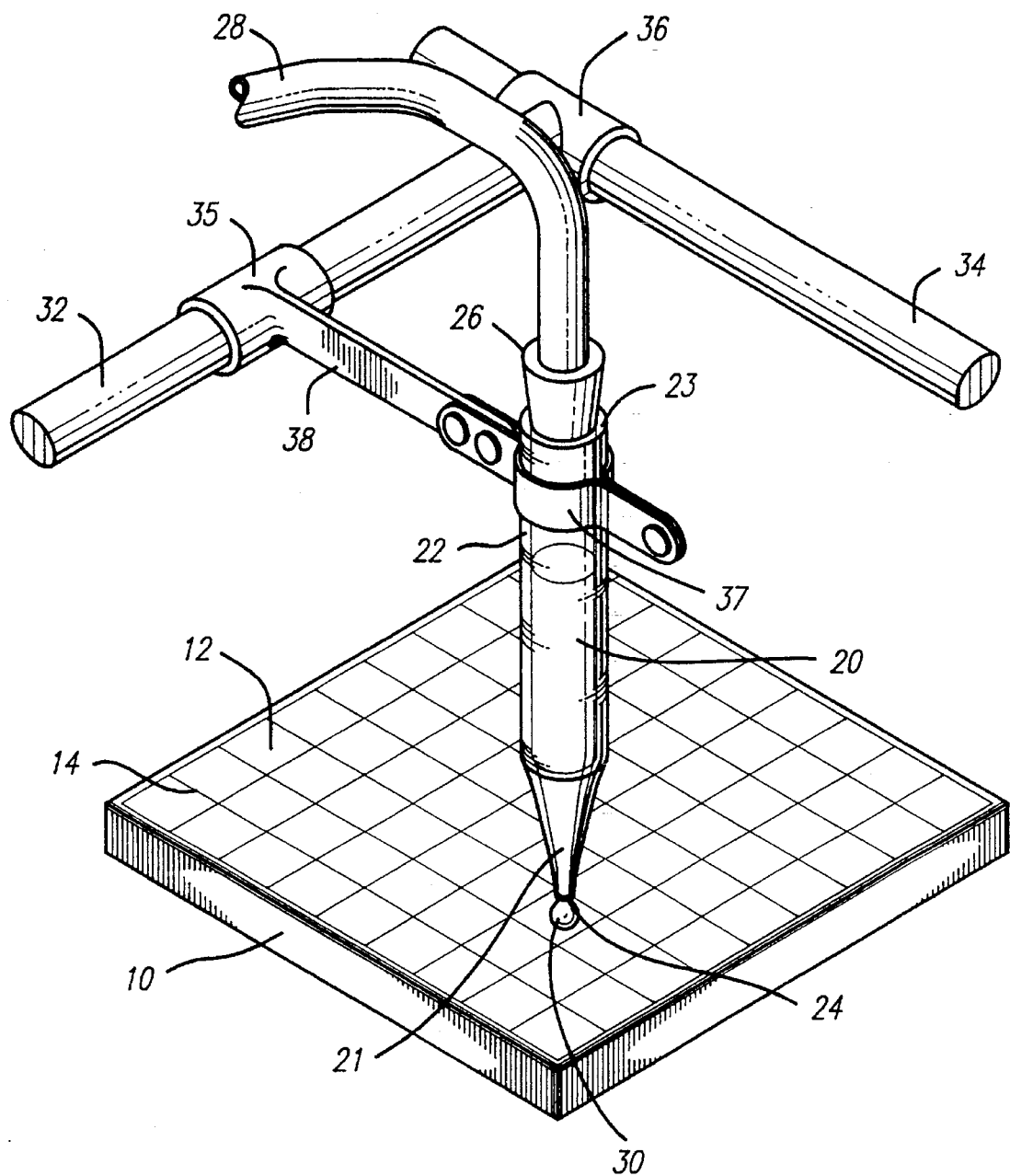
FIG. 1 illustrates a perspective view of a robotically manipulated micropipette used to spot biological probes onto an array.

Referring first to FIG. 1, a robotically manipulated micropipette is used to spot biological probes onto an array 10. The array 10 is partitioned into a plurality of individual cells 12, each of which receives a distinct type of probe. It is anticipated that the array 10 have a high number of cells 12, such as on the order of one thousand, though a smaller number of cells is illustrated in FIG. 1 for exemplary purposes. The array 10 may be comprised of fused silica, or other such material common to microscope slides.

The individual cells 12 may be designated by use of a numerical coordinate system based on each cell's position relative to the x and y-axis directions. The individual cells 12 are partitioned by indices 14 that further aid in designation of the cells for evaluation of probe reactions. The indices 14 may be directly etched onto the surface of the array 10, or may be graphically applied to a separate structure onto which the array is disposed with the indices viewable through the transparent material of the array. Alternatively, the indices 14 may not be used on an actual array, but may be virtually superimposed by use of computer graphics.

A micropipette 20 is provided to convey a supply of the probe in solution to a particular cell 12 of the array 10. The micropipette 20 comprises a tube 22 which is open at both ends. A first end 21 of the tube 22 is drawn to a very small diameter providing a tip 24. The second end 23 of the tube 22 is open for filling with a reservoir of the probe in solution and for connection to a gas pressure source, as will be further described below. To dispense fluid volumes in the desired range of approximately one nanoliter, it is anticipated that the tube 22 have a diameter on the order of one millimeter, with the tip 24 drawn to a diameter on the order of ten microns.

Alternatively, the supply of the probe in solution may not be maintained within the micropipette 20, but may instead be held in an external vial (not shown) connected to the micropipette. By application of pressure or vacuum, a quantity of the probe in solution may be inhaled into the micropipette 20 for spotting onto the array 10. This way, the size of the micropipette 20 can be kept relatively small, and can be periodically refilled from the external vial.

The second end 23 of the tube 22 is coupled to a gas pressure line 28 that connects the micropipette 20 to a pressure source, such as a pump. A stopper 26 provides a seal between the gas pressure line 28 and the tube 22. Application of gas pressure through the line 28 forces a droplet 30 of the probe to be dispensed from the tip 24. The micropipette 20 may alternatively be an initially sealed ampule containing a supply of the probe in solution, which is punctured by the gas line 28 for usage. In such an embodiment, the ampule would be disposed once a spotting operation is complete.

The exterior of the micropipette 20 may be provided with a hydrophobic coating so that the dispensed liquid will remain in the form of a globule at the tip 24, and not tend to wick up the outer surface of the micropipette which would aggravate dispensing. To promote efficient drawing of the liquid from the micropipette 20 and the absorption of the liquid onto an individual cell 12 of the array 10, the surface area defined between the indices 14 may be provided with a hydrophilic coating. The indices 14 may also be provided with a hydrophobic coating to prevent undesired traveling of the probe to an adjacent cell 12.

Manipulation of the micropipette 20 is provided by a cartesian robot, shown symbolically in FIG. 1 as having an x-axis rail 32 and a y-axis rail 34. The x-axis rail 32 couples to the y-axis rail 34 at a movable y-axis joint 36, and travels in the y-axis direction by motion of the y-axis joint along the y-axis rail. An arm 38 extends from a movable x-axis joint 35 that is coupled to the x-axis rail 32, and travels in the x-axis direction by motion of the x-axis joint along the x-axis rail.

The micropipette 20 is mounted to an end of the arm 38 by use of a controllable clamp 37. The clamp 37 should be capable of selectively grasping the micropipette 20, and permit the replacement of the micropipette with a different one as desired. The y-axis rail 34 may be further movable in the z-axis direction by use of an additional rail and joint (not shown). The joints 36, 35 are movable relative to the respective axes by use of motors, gears or other such frictional engagements. Cartesian robots of this nature are known in the art, and are capable of precise movement to position the micropipette 20 over a desired cell 12. Alternatively, the micropipette 20 may remain in a fixed position, and the array 10 shuttled into a precise position below the micropipette.

Figures 2A, 2B, 2C:
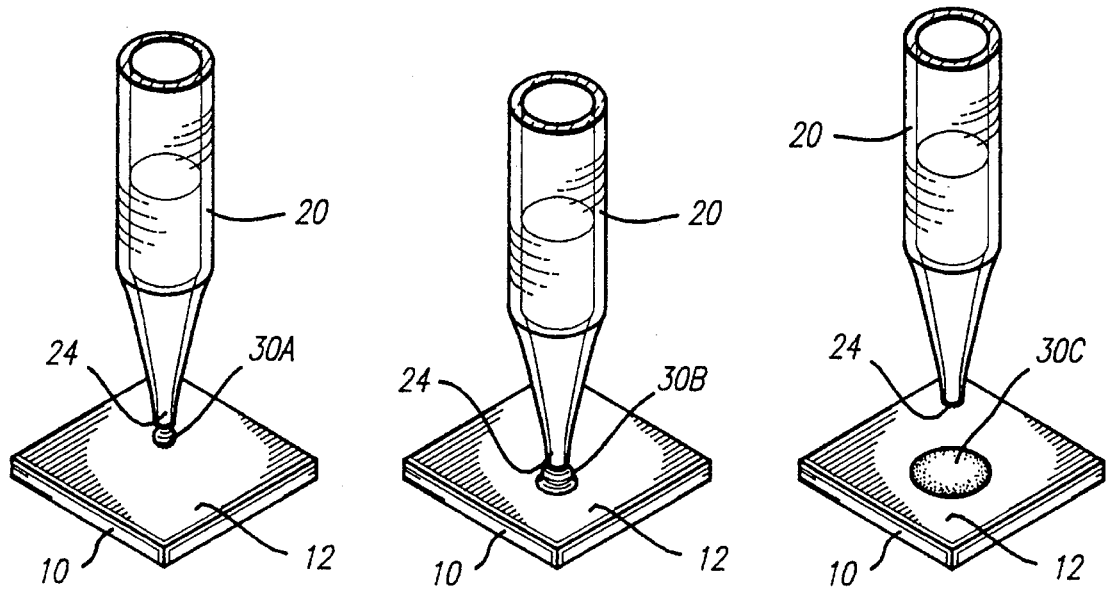
FIGS. 2A through 2C illustrate a tip of the micropipette brought into proximity with a selected location of an array for dispensing of a probe droplet.

Referring now to FIGS. 2A through 2C, a micropipette 20 is illustrated dispensing a single droplet 30 onto an individual cell 12 of an array 10. In FIG. 2A, the droplet 30A is produced at the tip 24 by application of gas pressure from the pressure source. Despite movement of the micropipette 20, the droplet 30A remains firmly affixed to the tip 24 by the surface tension of the liquid. In FIG. 2B, the droplet 30B is brought into contact with the cell 12 either by lowering the micropipette 20 or by raising the array 10. Once the droplet 30B contacts the hydrophilic surface of the cell 12, the droplet wicks completely onto the cell, as illustrated in FIG. 2C at 30C. Thereafter, the micropipette 20 is withdrawn from proximity to the array 10, reversing the previous motion of either the micropipette 20 or array 10.

Alternatively, the droplet 30 may be gravity dispensed onto the cell 12 of the array 10. After the droplet 30A is produced at the tip 24 of the micropipette 20 by application of gas pressure from the pressure source, as illustrated in FIG. 2A, the micropipette is rapidly withdrawn in a direction away from the cell 12. The rapid acceleration of the micropipette 20 causes the droplet 30 to become dislodged from the tip 24, enabling the droplet to fall to the cell 12 by force of gravity. This alternative approach avoids the risk of unintended contact between the tip 24 and the cell 12, which could potentially damage the tip and/or the array 10.

Figure 3:
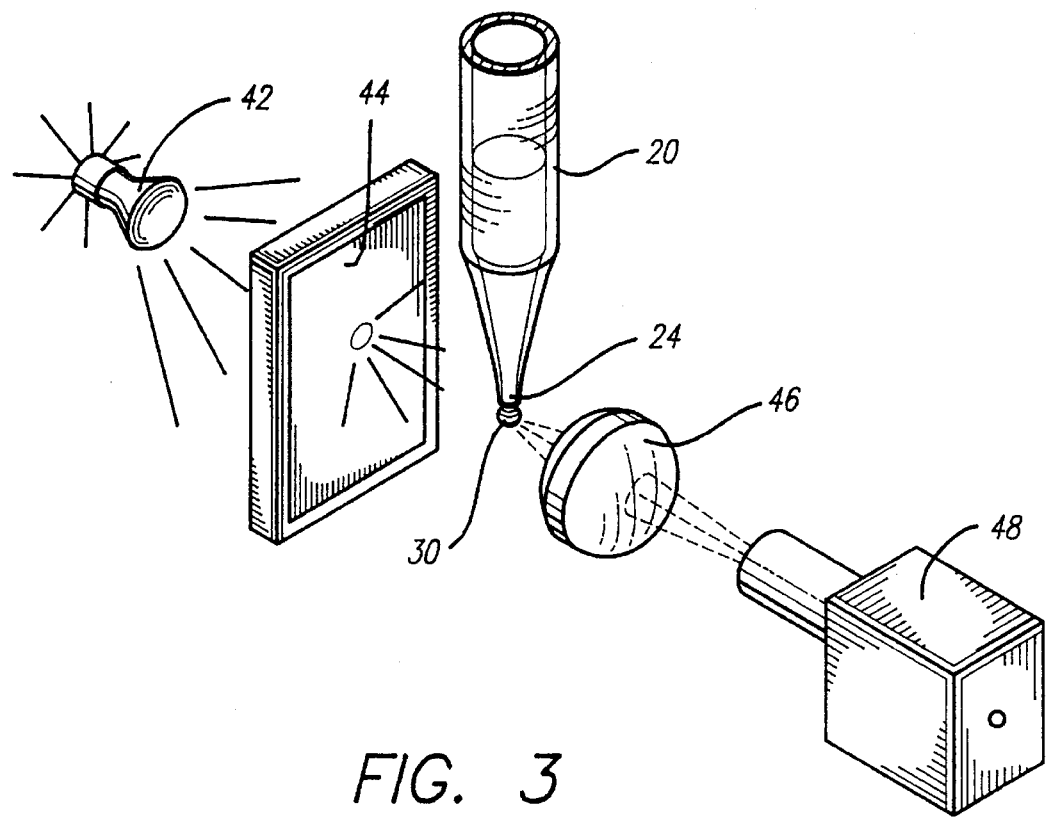
FIG. 3 illustrates a vision-assisted apparatus for estimating a volume measurement of the probe droplet.

Since the volume of liquid comprising the probe droplet 30 is critical, it is necessary that the volume be accurately gauged before it is dispensed onto the cell 12. FIG. 3 illustrates the elements of a vision-assisted system used to estimate the droplet volume. The vision-assisted system comprises a light source 42, a diffusing screen 44, an objective lens 46, and video imager 48. The light source 42 is preferably a light emitting diode (LED), but could also be a conventional incandescent light source. It is anticipated that the light source 42 would emit light having a blue or green color since the shorter wavelengths of light can yield higher resolution, although other visible and non-visible light spectra could also be advantageously utilized.

The diffusing screen 44 diffuses light emitted from the light source 42. Light scattered by the screen 44 transmits through the droplet 30, and is focused by the lens 46 onto the video imager 48. The video imager 48 may comprise a conventional video camera or charge coupled device. Accordingly, a two-dimensional image of the droplet 30 is transmitted onto the video imager 48, which converts the two-dimensional image into a signal representative of the volume of the droplet.

Figure 4:
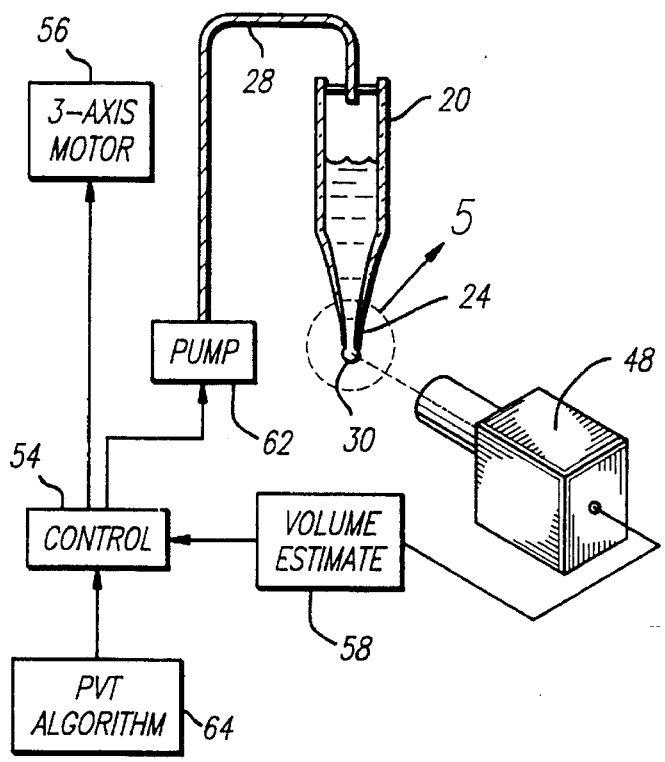
FIG. 4 is a block diagram of the vision-assisted apparatus of FIG. 3.

FIG. 4 is a block diagram illustrating the operation of the vision-assisted system. A central control device 54 directs the operation of a three-axis motor 56 and a pump 62. The control device 54 receives information from a volume estimating device 58 and an algorithm 64. As described above, the micropipette 20 is manipulated into position in the x and y-axis directions by use of a cartesian robot, or other such mechanism. The micropipette 20 is further lowered and raised relative to the array in the z-axis direction to dispense the droplet 30. The three-axis motor 56 receives control signals from the control device 54 to manipulate the micropipette 20 in the desired manner.

The pump 62 provides the pressure source described above that applies pressure through the gas line 28 to force the droplet 30 through the tip 24. Since gas pressure (P) is proportional to the product of volume (V) and temperature (T), the amount of pressure necessary to discharge a droplet of predetermined volume can be estimated. The algorithm 64 defines the precise relationship between pressure, volume and temperature, and provides data to the control device 54 to direct the pump 62 to supply the required amount of pressure for a period of time to the micropipette 20. Alternatively, the data values determined by the algorithm could comprise a table stored in a memory device, such as a computer memory. After providing the required pressure to the micropipette 20 to produce the droplet, it may be necessary to reverse the pressure slightly in order to prevent the droplet from growing in size beyond the desired volume, and to hold the droplet in place at the tip of the micropipette.

While it may be possible to operate the above described system effectively using only the control device 54, algorithm 64 and pump 62, vision-assistance provides feedback to the control device necessary to increase the droplet volume accuracy and repeatability. The video imager 48 produces a two-dimensional image of the droplet during its formation and provides an associated signal to a volume estimator 58. In turn, the volume estimator 58 provides a signal representative of the droplet volume to the control device 54. The volume estimate could be used to precisely control the turn-off time for the pump 62, rather than relying entirely on the algorithm data to define the timing of the turn-off signal. Alternatively, the volume estimate could be used to verify the accuracy of the algorithm data, which would be periodically revised by the volume estimate.

Figure 5:
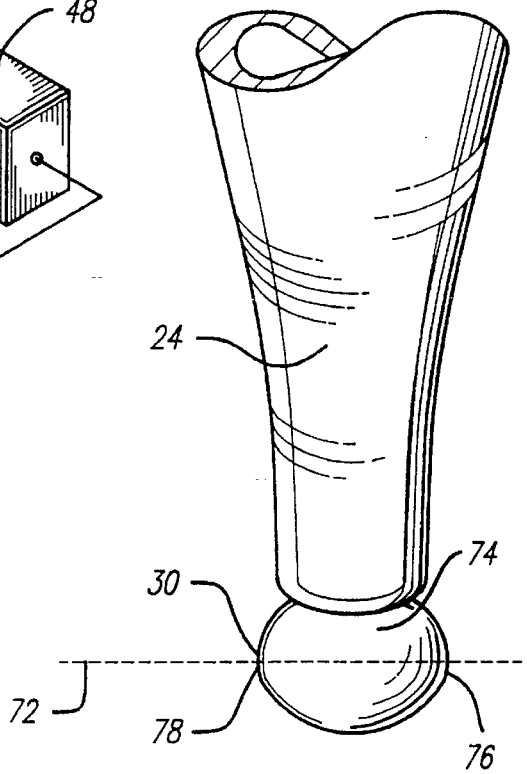
FIG. 5 is an enlarged view of a probe droplet affixed to a tip of the micropipette.

The determination of the droplet volume estimate is illustrated with respect to FIGS. 5 and 6A through 6C. FIG. 5 illustrates an enlarged view of a tip 24 of the micropipette of FIG. 4. The tip 24 has a droplet 30 held in place by the surface tension of the droplet. The droplet is presumed to form a generally spherical shape due to the surface tension of the liquid. In actuality, the droplet is not perfectly spherical; nevertheless, the spherical shape approximates the actual shape of the droplet sufficiently to make an accurate volume determination.

In FIG. 5, an imaginary centerline 72 is defined at a fixed distance below the bottom edge of the tip 24, which divides the droplet into presumably equal hemispheres. Light transmitted through the screen 44 passes through the droplet 30 and is received by the video imager 48. The curvature of the droplet causes light at the circumference of the droplet to refract, thus the transmittance of light is greater at the center 74 of the droplet than at the respective edges 76, 78. The refraction of light provides a convenient measure to determine the diameter of the sphere that approximates the droplet.

Figure 6A:
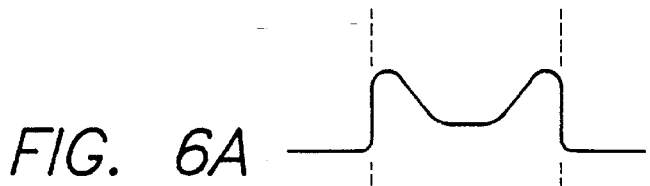
FIGS. 6A through 6C illustrates signals corresponding to diameter measurements of the droplet of FIG. 5.
Figure 6B:
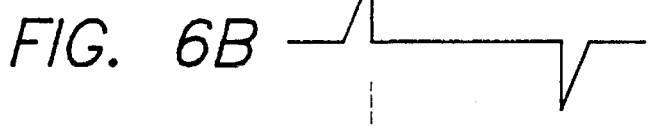
Figure 6C:

Referring to FIGS. 6A through 6C, the light refraction is converted to a diameter value. The measured light refraction is illustrated in FIG. 6A, with the greatest amount of refraction occurring at the edges 76, 78, and the least amount of refraction occurring at the center 74. The refraction curve of FIG. 6A is differentiated to produce the curve of FIG. 6B to more accurately define the edge points. The absolute value of the differentiated curve is illustrated in FIG. 6C. The absolute value curve provides clear indication of the edge points for the droplet, and can be subtracted to provide a diameter measurement (D).

Alternatively, the video imager 48 could make a plurality of raster scans adjacent to the imaginary centerline 72. Refraction values from each of the raster scans could be averaged or differentiated to determine a mean diameter measurement (D). This technique would allow for slight variations in droplet shape due to external factors, such as temperature and vibration.

The diameter measurement (D) can then be readily converted to a volume (V) value by the relation $4\pi r^3/3$, where r is radius (D/2). Alternatively, the video imager 48 could simply convert the two-dimensional image of the droplet into a signal representative of the area of the image ($\pi r^2$). By calculating the integral of the signal and multiplying by four, a volume value (V) can also be determined.

The video imager 48 can further be used to provide precise positional control information to the control device 54. The video imager 48 can accurately detect the precise position of the tip 24 of the micropipette 20 relative to the indices 14 that partition the array 10. Differences between actual tip position and desired tip position can be converted to control signals provided by the control device 54 to the three-axis motor 56. As with the volume estimation function, the vision-assistance can be used in a real-time manner to control the tip position. In this configuration, the video imager 48 would identify the precise moment that the tip 24 has reached the proper position in order to command the three-axis motor 56 to stop moving. Alternatively, the vision-assistance can be used merely as a spot check verification of position accuracy, and for periodic correction of the algorithm values that control the command signals provided by the control device 54.

Having thus described a preferred embodiment of a method and apparatus for manufacturing biological probe arrays using vision-assisted micropipetting, it should be apparent to those skilled in the art that certain advantages of the within system have been achieved. Accordingly, the invention is defined by the following claims.

What is claimed is:

1. An apparatus for spotting a biological probe onto an array, comprising:

a micropipette containing a quantity of biological probe in solution, and means for manipulating said micropipette to a selected location within an array;

a pressure source in communication with said micropipette, a droplet of said biological probe being provided at an open tip of said micropipette by application of pressure from said pressure source;

means for estimating a volume measurement of said droplet; and means for discontinuing application of said pressure upon reaching a predetermined volume for said droplet.

2. The apparatus of claim 1, wherein said estimating means further comprises means for monitoring formation of said droplet.

3. The apparatus of claim 2, wherein said monitoring means further comprises a video imager.

4. The apparatus of claim 1, further comprising means for estimating a position of said micropipette.

5. The apparatus of claim 1, wherein said micropipette further comprises a hydrophobic surface.

6. The apparatus of claim 2, wherein said monitoring means further comprises means for forming a two-dimensional image of said droplet, and means for converting the two-dimensional image to a signal representative of a diameter of said droplet.

7. A method for spotting a biological probe onto an array, comprising the steps of:

manipulating a micropipette containing a quantity of a biological probe in solution to a position above a selected location within an array;

pressurizing the micropipette sufficiently to produce a droplet of said biological probe at an open tip of said micropipette;

monitoring formation of said droplet simultaneously with said pressurizing step;

estimating a volume measurement of said droplet;

discontinuing said pressurizing step upon reaching a predetermined volume for said droplet; and dispensing said droplet onto said selected location.

8. The method of claim 7, wherein said monitoring step further comprises forming a two-dimensional image of said droplet.

9. The method of claim 7, wherein said estimating step further comprises converting the two-dimensional image to a signal representative of a diameter of said droplet.

10. The method of claim 9, wherein said converting step comprises;

generating a signal from said two-dimensional image representative of refraction of light transmitted through said droplet;

differentiating said generated signal;

determining an absolute value of said differentiated signal; and subtracting between a leading edge of a first end of the absolute value signal and a trailing edge of a second end of the absolute value signal.

11. The method of claim 9, wherein said converting step comprises;

generating a plurality of raster scans of said droplet;

determining respective values representative of refraction of light transmitted through said droplet for each of said raster scans; and determining an average of said respective refraction values.

12. The method of claim 7, further comprising the step of estimating position of said micropipette.

13. The method of claim 7, wherein said dispensing step further comprises the steps of:

bringing the micropipette in proximity with the selected position of the array until the droplet contacts the array, causing the droplet to burst; and withdrawing the micropipette from proximity with the array.

14. The method of claim 7, wherein said dispensing step further comprises the steps of:

bringing the micropipette in proximity with the selected position of the array; and withdrawing the micropipette from proximity with the array with sufficient rapidity to cause the droplet to dislodge from the tip.

15. A method for spotting a biological probe onto an array, comprising the steps of:

manipulating a micropipette containing a quantity of a biological probe in solution to a position above a selected location within an array;

producing a droplet of said biological probe at an open tip of said micropipette;

determining a volume measurement of said droplet by use of a visual sensor; and when said droplet reaches a predetermined volume dispensing said droplet onto said selected location.

16. The method of claim 15, wherein said determining step further comprises forming a two-dimensional image of said droplet, and converting the two-dimensional image to a signal representative of a diameter of said droplet.

17. The method of claim 16, wherein said converting step comprises the steps of:

generating a signal from said two-dimensional image representative of refraction of light transmitted through said droplet;

differentiating said generated signal;

determining an absolute value of said differentiated signal; and subtracting between a leading edge of a first end of the absolute value signal and a trailing edge of a second end of the absolute value signal.

18. The method of claim 16, wherein said converting step comprises the steps of:

generating a plurality of raster scans of said droplet;

determining respective values representative of refraction of light transmitted through said droplet for each of said raster scans; and determining an average of said respective refraction values.

19. The method of claim 15, wherein said dispensing step further comprises the steps of:

bringing the micropipette in proximity with the selected position of the array until the droplet contacts the array, causing the droplet to burst; and withdrawing the micropipette from proximity with the array.

20. The method of claim 15, wherein said dispensing step further comprises the step of:

bringing the micropipette in proximity with the selected position of the array; and withdrawing the micropipette from proximity with the array with sufficient rapidity to cause the droplet to dislodge from the tip.

* * * * *